US008686172B2

(12) United States Patent
Hupp et al.

(10) Patent No.: US 8,686,172 B2
(45) Date of Patent: *Apr. 1, 2014

(54) ACTIVATION OF POROUS MOF MATERIALS (71) Applicant: Northwestern University, Evanston, IL (US)

(72) Inventors: Joseph T. Hupp, Northfield, IL (US); Omar K. Farha, Morton Grove, IL (US)

(73) Assignee: Northwestern University, Evansville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/866,194

(22) Filed: Apr. 19, 2013

(65) Prior Publication Data

US 2013/0237412 A1 Sep. 12, 2013

Related U.S. Application Data

(63) Continuation of application No. 12/928,321, filed on Dec. 8, 2010, now Pat. No. 8,426,624.

(60) Provisional application No. 61/283,875, filed on Dec. 10, 2009.

(51) Int. Cl.
*C07F 3/06* (2006.01)

(52) U.S. Cl.
USPC ........................................................ 556/121

(58) Field of Classification Search
USPC ........................................................ 556/121
See application file for complete search history.

(56) References Cited

U.S. PATENT DOCUMENTS 8,426,624 B2 * 4/2013 Hupp et al. ................... 556/121

OTHER PUBLICATIONS

Kaye et al., Journal of American Chemical Society, vol. 129, No. 46, pp. 14176-14177 (2007).*
Britt et al., Inorganic Chemistry, vol. 49, No. 14, pp. 6387-6389 (2010).
O.M. Yaghi et al., "Synthetic Strategies, Structure Patterns, and Emerging Properties in the Chemistry of Modular Porous Solids," Acc. Chem. Res. 1998, 31, pp. 474-484.
R.Q. Snurr et al., "Prospects for Nanoporous Metal-Organic Materials in Advanced Separations Processes," AIChE 2004, 50, pp. 1090-1095.
B. Chen et al., "High $H_2$ Adsorption in a Microporous Metal-Organic Framework with Open Metal Sites," Agnew. Chem. Int. Ed., 2005, 44, pp. 4745-4749.
M. Latroche et al., "Hydrogen Storage in the Giant-Pore Metal-Organic Frameworks MIL-100 and MIL-101," Angew. Chem. Int. Ed., 2006, 45, pp. 8227-8231.
Z. Wang et al., "Tandem Modification of Metal-Organic Frameworks by a Postsynthetic Approach," Agnew. Chem. Int. Ed., 2008, 47, pp. 4699-4702.

(Continued)

*Primary Examiner* — Porfirio Nazario Gonzalez
(74) *Attorney, Agent, or Firm* — The Marbury Law Group PLLC (57) ABSTRACT

A method for the treatment of solvent-containing MOF material to increase its internal surface area involves introducing a liquid into the MOF in which liquid the solvent is miscible, subjecting the MOF to supercritical conditions for a time to form supercritical fluid, and releasing the supercritical conditions to remove the supercrital fluid from the MOF. Prior to introducing the liquid into the MOF, occluded reaction solvent, such as DEF or DMF, in the MOF can be exchanged for the miscible solvent.

14 Claims, 4 Drawing Sheets

(56) References Cited

OTHER PUBLICATIONS

C.J. Kepert et al., "Zeolite-like Crystal Structure of an Empty Microporous Molecular Framework," Chem. Commun., 1999, pp. 375-376.

S.H. Cho et al., "A Metal-Organic Framework Material That Functions as an Enantioselective Catalyst for Olefin Epoxidation," Chem. Commun., 2006, pp. 4135-4137.

Y.S. Bae et al., "Carborane-based Metal-Organic Frameworks as Highly Selective Sorbents for $CO_2$ Over Methane," Chem. Commun., 2008, pp. 4135-4137.

G. Ferey, "Hybrid Porous Solids: Past, Present, Future," Chem. Soc. Rev., 2008, 37, pp. 191-214.

Reichenauer et al., "Extracting the Pore Size Distribution of Compliant Materials from Nitrogen Adsorption," Colloids and Surfaces A, 2001, 187-188, pp. 41-50.

A. Cooper, "Polymer Synthesis and Processing Using Supercritical Carbon Dioxide," J. Mater. Chem., 2000, 10, pp. 207-234.

D.J. Collins et al., "Hydrogen Storage in Metal-Organic Frameworks," J. Mater. Chem., 2007, 17, pp. 3154-3160.

G. Reichenaur et al., "Nitrogen Sorption in Aerogels," J. Non-Cryst. Solids, 2001, 285, pp. 167-174.

T. Duren et al., "Calculating Geometric Surface Areas as a Characterization Tool for Metal-Organic Organic Frameworks," J. Phys. Chem. C, 2007, 111, pp. 15350-15356.

L. Bastin et al., "A Microporous Metal-Organic Framework for Separation of $CO_2/N_2$ and $CO_2/CH_4$ by Fixed-Bed Adsorption," J. Phys. Chem. C, 2008, 112, pp. 1575-1581.

E.Y. Lee et al., Multifunctionality and Crystal Dynamics of a Highly Stable, Porous Metal-Organic Framework $[Zn_4O (NTB)_2]$, J. Am. Chem. Soc., 2005, 127, pp. 6374-6381.

C.D. Wu et al., "A Homochiral Porous Metal-Organic Framework for Highly Enantioselective Heterogeneous Asymmetric Catalysis," J. Am. Chem. Soc., 2005, 127, pp. 8940-8941.

M. Dinca et al., Strong $H_2$ Binding and Selective Gas Adsorption within the Microporous Coordination Solid $Mg_3 (O_2C-C_{10}H_6-CO_2)_3$, J. Am. Chem. Soc., 2005, 127, pp. 9376-9377.

M. Dinca et al., Hydrogen Storage in a Microporous Metal-Organic Framework with Exposed $Mn^{2+}$ Coordination Sites, J. Am. Chem. Soc., 2006, 128, pp. 16876-16883.

K. L. Mulfort et al., "Chemical Reduction of Metal-Organic Framework Materials as a Method to Enhance Gas Uptake and Binding," J. Am. Chem. Soc., 2007, 129, pp. 9604-9605.

Z. Wang et al., "Postsynthetic Covalent Modification of a Neutral Metal-Organic Framework," J. Am. Chem. Soc., 2007, 129, pp. 12368-12369.

O.K. Farha et al., "Synthesis and Hydrogen Sorption Properties of Carborane Based Metal-Organic Framework Materials," J. Am. Chem. Soc., 2007, 129, pp. 12680-12681.

S. Horike et al. "Size-Selective Lewis Acid Catalysis in a Microporous Metal-Organic Framework with Exposed $Mn^{2+}$ Coordination Sites," J. Am. Chem. Soc., 2008, 130, pp. 5854-5855.

K. K. Tanabe et al., "Systematic Functionalization of a Metal-Organic Framework via a Postsynthetic Modification Approach," J. Am. Chem. Soc., 2008, 130, pp. 8508-8517.

F. Nouar et al., "Supermolecular Building Blocks (SBBs) for the Design and Synthesis of Highly Porous Metal-Organic Frameworks," J. Am. Chem. Soc., 2008, 130, pp. 1833-1835.

Y.S. Bae et al., "Separation of $CO_2$ from $CH_4$ Using Mixed-Ligand Metal-Organic Frameworks," Langmuir, 2008, 24, pp. 8592-8598.

M. Eddaoudi et al., "Systematic Design of Pore Functionality in Isoreticular MOFs and their Application in Methane Storage," Science 2002, 295, pp. 469-472.

J. A. Lubguban et al., "Supercritical $CO_2$ Extraction of Porogen Phase: An Alternative Route to Nanoporous Dielectrics," J. Mater. Res. 2004, 19, pp. 3224-3233.

\* cited by examiner

ACTIVATION OF POROUS MOF MATERIALS

This application claims benefits and priority of U.S. provisional application Ser. No. 61/283,875 filed Dec. 10, 2009, the disclosure of which is incorporated herein by reference.

CONTRACTUAL ORIGIN OF THE INVENTION

This invention was made with government support under Grant No. DE-FG02-01ER15244 awarded by the Department of Energy. The Government has certain rights in the invention.

FIELD OF THE INVENTION

The present invention relates to treatment of metal-organic framework (MOF) materials to increase their internal surface area to render them more active to gas adsorption.

BACKGROUND OF THE INVENTION

Metal-organic frameworks (MOFs) (reference 1) have emerged as attractive materials for a remarkably wide range of potential applications, including chemical separations (reference 2), size-selective molecular catalysis (reference 3), and chemical fuel storage and release (reference 4). Among the material properties favoring these particular applications are permanent microporosity and large internal surface areas. Unfortunately, the surface areas attained experimentally are often less than anticipated from computational studies or single-crystal X-ray structural studies (reference 5). Furthermore, they can differ substantially from laboratory to laboratory. The disparities and discrepancies have most often been attributed to channel collapse upon solvent removal or channel blockage due to solvent retention (reference 6). In many instances, porosity can be recovered and surface areas can be increased by exchanging the MOF-incorporated solvent remaining from synthesis (referred to later herein as occluded reaction solvent) for a lower boiling point solvent and then removing the solvent under relatively mild conditions (reference 7). Nevertheless, applicants have noted that the liquid solvent exchange strategy still occasionally fails to elicit MOF microporosity or, more commonly, succeeds in enabling access to the internal surface area of a given MOF, but to a lesser extent than anticipated from computations.

SUMMARY OF THE INVENTION

The present invention relates to a method for treating solvent-containing metal-organic framework (MOF) materials with liquid and supercritical fluid, such as for example, liquid carbon dioxide and then supercritcal carbon dioxide, to substantially increase internal surface area.

In an illustrative embodiment of the present invention, the method involves introducing liquid carbon dioxide into the MOF material in which liquid carbon dioxide the MOF solvent is miscible and then subjecting the MOF material to supercritical conditions to form supercritical carbon dioxide, and then releasing the supercritical conditions to remove the carbon dioxide from the MOF material. Prior to introducing the liquid carbon dioxide into the MOF material, occluded reaction solvent, such as diethylformamide, dimethylformamide or other solvent, in the MOF material can be exchanged for the miscible solvent, such as ethanol, if necessary depending upon the liquid subsequently employed.

The present invention is advantageous in that processing pursuant to the invention can result in substantial, or in some cases spectacular (up to 1200%), increases in gas-accessible surface area. Maximization of surface area is key to the optimization of MOF materials for many potential applications.

Advantages and benefits of the present invention will become more readily apparent from the following detailed description of the invention taken with the following drawings.

DETAILED DESCRIPTION OF THE INVENTION

The present invention provides a method of treating a solvent-containing metal-organic framework (MOF) material first with a liquid in which a solvent residing in the MOF material is miscible and then under supercritical conditions for the liquid followed by release of supercritical conditions in a manner to substantially increase internal surface area of the material. The solvent can be occluded reaction solvent remaining from preparation of the MOF material, or a different solvent that is exchanged for the occluded reaction solvent and is compatible with later treatment steps of the invention to effect supercritical drying.

In practicing an illustrative embodiment, the method involves introducing a solvent-miscible liquid into the MOF material, subjecting the MOF material to supercritical conditions to form supercritical fluid, and releasing the supercritical conditions to remove the supercritcal fluid. As mentioned, the solvent can be occluded reaction solvent that remains in the MOF structure from the synthesis to produce the material. For example, the occluded reaction solvent can be selected from the group consisting of diethylformamide, dimethylformamide, and other solvent used in synthesis of the MOF material. Alternatively, the occluded reaction solvent can be exchanged prior to introduction of the liquid with another solvent that is compatible and miscible in the liquid to be introduced into the MOF material. Thus, this latter embodiment envisions prior to introducing the liquid into the MOF material, exchanging occluded reaction solvent in the MOF material for the miscible solvent. The miscible solvent can comprise ethanol for purposes of illustration and not limitation.

In practicing an illustrative embodiment of the invention, liquid carbon dioxide is introduced into the solvent-containing MOF material and then supercritical conditions are imposed on the MOF material in a supercritcal point dryer or other apparatus so as to exceed the critical point of carbon dioxide. Thereafter, the supercritical conditions are released by slowly venting the supercritical point dryer chamber to ambient atmosphere to remove the supercritical fluid (e.g. supercritical carbon dioxide). Practice of the invention is not limited to carbon dioxide since other liquids and corresponding supercritical fluids can be used.

The following Examples are offered to further illustrate but not limit the invention.

EXAMPLES

The examples involve treating four MOF materials comprising dicarboxylated organic ligands as struts and Zn(II)-containing clusters as nodes. As will be shown below, the method of invention is capable of very substantially enhancing access to MOF internal surface area relative to other treatments that involve either (a) thermally assisted evacuation of the solvent used for synthesis (DMF or DEF) ("conventional activation") or (b) liquid solvent exchange (e.g., DMF ↔ CHCl$_3$: DEF ↔ THF) followed by pore evacuation at moderate temperature (where DMF=dimethylformamide, DEF=diethylformamide, THF=tetrahydrofuran).

Figure 1A:
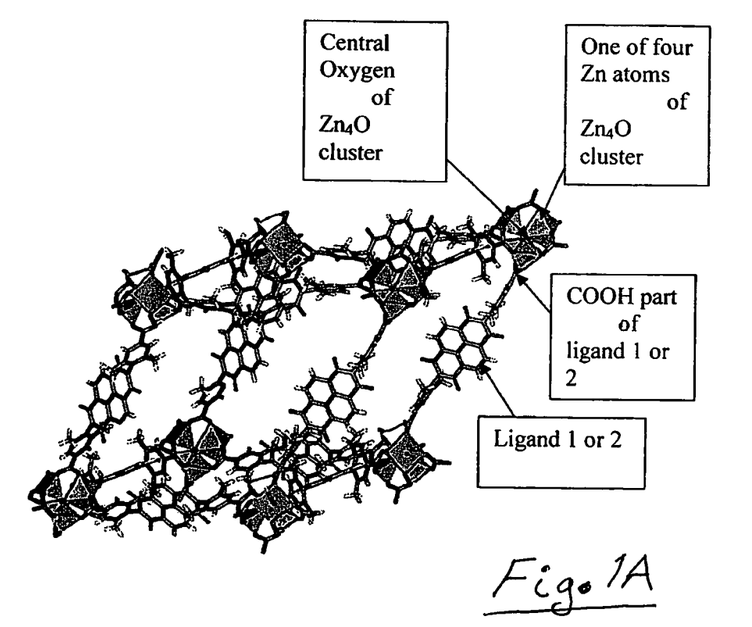
FIG. 1A is a crystallographically derived structure of MOF 5. For clarity, disordered DEF molecules and coordinated DEF molecules are omitted.
Figure 1B:
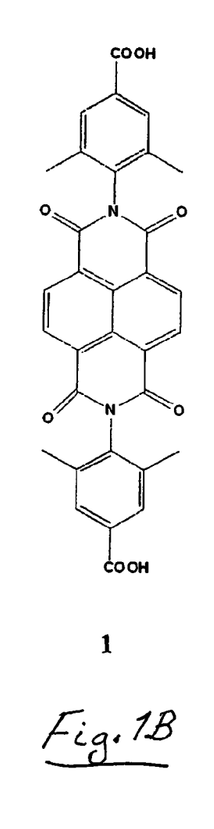
FIGS. 1B, 1C, 1D, and 1E illustrate ligands 1, 2, 3, and 4.
Figure 1C:
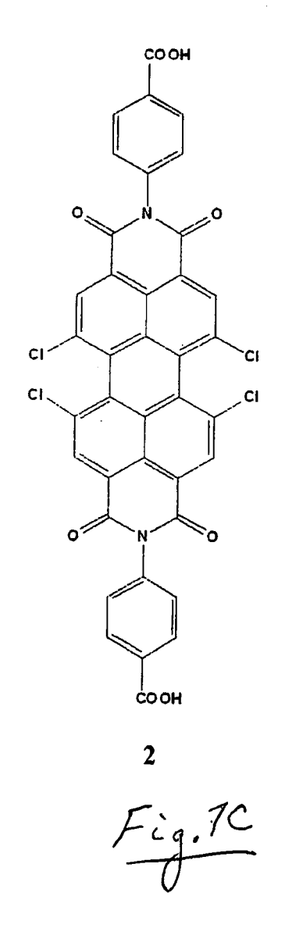

The first of the four investigated MOF materials was obtained by solvothermal synthesis from a DEF solution of ZnNO$_3$.6H$_2$O and a napthalenediimide-containing ligand, 1. Details of the solvothermal synthesis are set forth below in the "Synthesis" section. FIG. 1A shows the structure of the resulting channel-containing MOF material 5. The nodes of 5 consist of Zn$_4$O clusters, coordinated by carboxylates in both a mono- and bidentate fashion. Each node is also coordinated by one water and two DEF molecules. In contrast to the cubic frameworks typically obtained with these clusters, the unusual coordination produces a canted rhombohedral framework.

Single-crystal X-ray structure (see Synthesis section) indicates that the channels of "as-synthesized" MOF 5 are fully occupied, presumably by disordered DEF. Inclusion of pairs of methyl groups on the phenyl carboxylate units proved essential for formation of a crystalline coordination polymer. Attempts to prepare MOFs using analogues of 1 lacking one or both methyl groups yielded only amorphous solids. In the crystal structure of MOF 5, the methyl groups render the napthelendiimide geometrically orthogonal to the phenyl carboxylate.

A similar solvothermal synthesis in DMF, but with ligand 2 rather than ligand 1, yielded a red solid, MOF 6. While applicants were unable to obtain a suitable single crystal for X-ray structural determination, powder X-ray diffraction (PXRD) measurements revealed that the material is crystalline. $^1$H NMR measurements of a sample of 6 that had been thermally evacuated and then dissolved in D$_2$SO$_4$ showed the presence only of 2 and a trace amount of DMF.

Thermal gravimetric analysis (TGA) of MOF 5 indicated a ca. 35% mass decrease (solvent loss) upon heating to 250° C., a result consistent with the porosity implied by the X-ray structure and suggesting substantial internal surface area. TGA measurements of MOF 6 showed a 17% mass loss upon heating to 300° C. (the framework itself is stable to ca. 400° C.). The diminished solvent capacity despite the larger strut size is suggestive of network catenation, the formation of a 2D rather than 3D structure, or both.

Figure 2A:
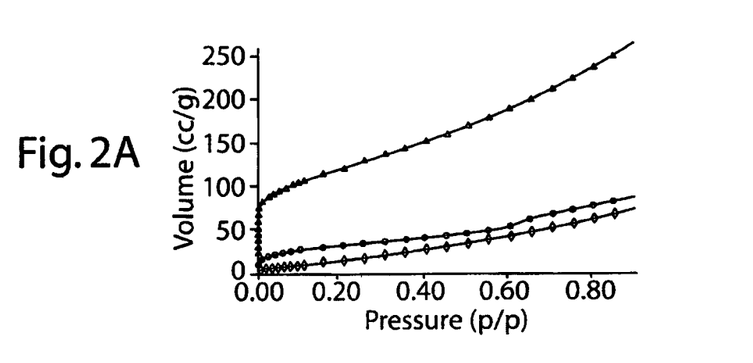
FIG. 2A shows 77K $N_2$ adsorption isotherms of MOF 5 following activation by ScD (supercritical drying) (top curve), following exchange with THF and evacuation at 25° C. (middle curve), or following conventional activation at 110° C. (bottom curve).
Figure 2B:
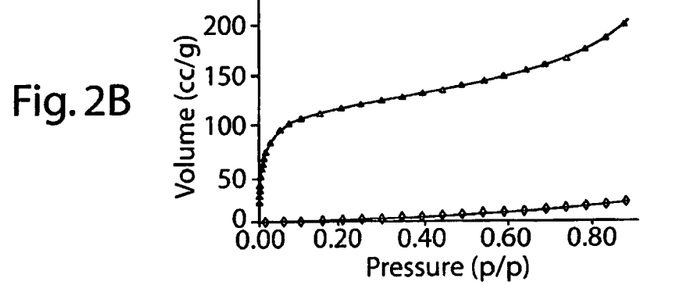
FIG. 2B shows 77K $N_2$ isotherms of MOF 6 following ScD activation (top curve), following exchange with chloroform followed by evacuation at 25° C. (bottom curve), or following traditional activation 110° C. (bottom, overlap curve).

In contrast to the implications from X-ray and/or TGA measurements, N$_2$ adsorption studies (77 K) indicate negligible accessible surface areas for either MOF 5 or 6, following conventional thermal activation (FIG. 2 and Table 1). Solvent exchange with 6 (CHCl$_3$) yields no meaningful improvement, while solvent exchange with 5 (THF) yields a modest Brunauer-Emmet-Teller (BET) surface area of 135 m$^2$/g.

In order to improve upon these gas-accessible surface area results, the MOF materials were treated using supercritical drying (ScD) as an activation method pursuant to the present invention. The ScD treatment is advantageous due to its low cost of CO$_2$(g) and availability of a critical point dryer.

Briefly, the ScD treatment involved exchanging the occluded reaction solvent remaining from MOF synthesis with EtOH (ethanol) solvent (which is miscible with CO$_2$) and then with liquid CO$_2$. The sample was then taken above the carbon dioxide critical point (T=31° C.; P=73 atm), held for 30 min, and finally, slowly vented to ambient atmosphere for 18 hours. As illustrated in FIG. 2, the results are striking: the N$_2$-accessible surface area increases to 400 m$^2$/g, for MOF 5 (3-fold increase) and 430 m$^2$/g for MOF 6 (12-fold increase).

Details of the supercritical drying treatment are as follows. The MOF materials were evacuated with supercritical CO$_2$ in a Tousimis™ Samdri® PVT-30 critical point dryer. Prior to drying, the DMF/DEF solvated MOF samples were soaked in absolute ethanol (EtOH), replacing the soaking solution every 24 hrs for 72 hrs, to exchange the occluded reaction solvent for EtOH. After the 72 hr exchange process was complete the ethanol-containing samples were placed inside the dryer and the ethanol was exchanged with (miscible in) CO$_{2\,(L)}$ over a period of 6 hrs. During this time the liquid CO$_2$ was vented under positive pressure for five minutes each hour. The rate of venting of CO$_{2\,(L)}$ was always kept below the rate of filling so as to maintain a full drying chamber. After 6 hrs of venting and soaking with CO$_{2\,(L)}$ the chamber was sealed and the temperature was raised to 40° C. This brought the dryer chamber pressure to around 1300 psi above the critical point of CO$_2$. The chamber was held above the critical point for 1 hour at which point the chamber was slowly vented over the course of 15-18 hrs to ambient atmosphere to remove the supercritical carbon dioxide and miscible solvent. The dried samples were placed in sealed containers and stored in a desiccator or tested for nitrogen adsorption immediately.

TABLE 1

Nitrogen-Accessible Surface Areas (m$^2$/g) of Various Framework Materials as a Function of Method of Pore Evacuation

| Material | conventional thermal evacuation | CHCl$_3$ or THF Exchange | ScD |
|---|---|---|---|
| IRMOF-3 | 10 | 1800 | 2850 |
| IRMOF-16 | — | 470 | 1910 |
| 5 | 5 | 135 | 400 |
| 6 | 5 | 36 | 430 |

Figure 1D:
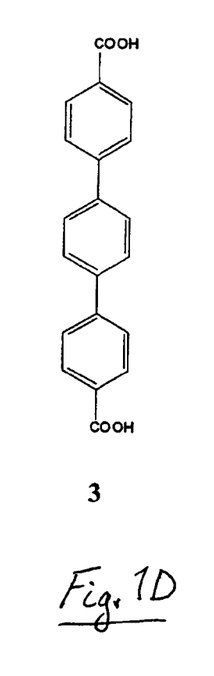
Figure 1E:
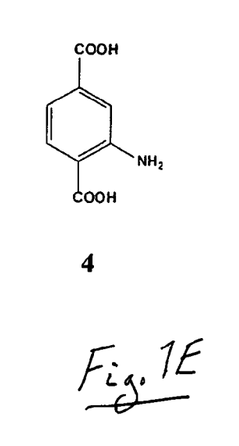

In view of the above favorable increase in internal surface areas of the MOF materials, tests were conducted on noncatenated, cubic, 'isoreticular' MOF materials constructed from ligand 4 (FIG. 1E) designated IRMOF-3 and ligand 3 (FIG. 1D) designated IRMOF-16 as described in the "Synthesis" section. IRMOF-3 has attracted considerable recent attention because of its susceptibility to postsynthetic covalent modification via the available amine group (references 9a-9c).

Figure 3A:
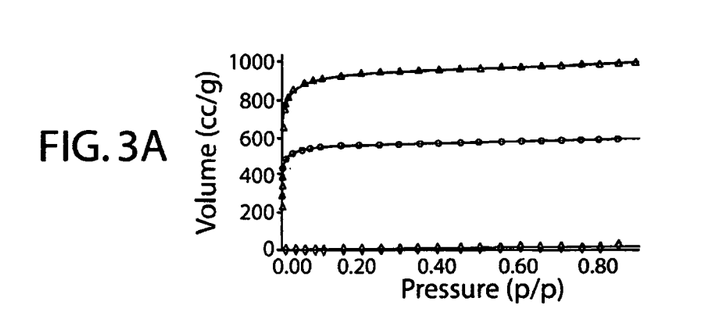
FIG. 3A shows 77 K $N_2$ isotherms of IRMOF-3 following ScD activation (top curve), following exchange with $CHCl_3$ followed by evacuation at 25° C. (middle curve), or following conventional activation at 100° C. (bottom curve).
Figure 3B:
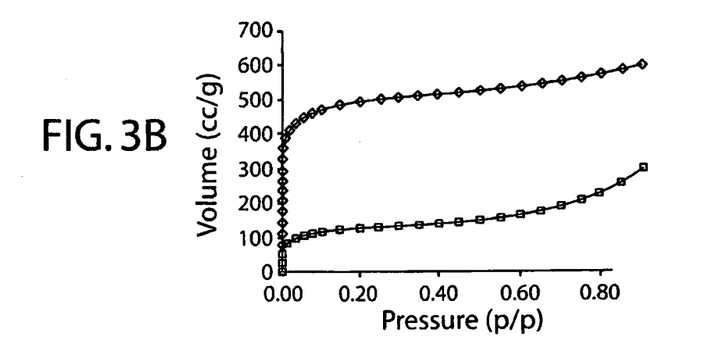
FIG. 3B shows 77 K $N_2$ isotherms of IRMOF-16 following ScD activation (top curve) or following exchange with $CHCl_3$ followed by activation at 25° C. (bottom curve).

For IRMOF-3, activation via solvent exchange (DMF ↔ CHCl$_3$) yielded a surface area of 1800 m$^2$/g. ScD activation pursuant to the invention increases the N$_2$ accessible surface area to 2850 m$^2$/g (FIG. 3). For IRMOF-16 there are no previous reports of surface area. From FIG. 3, the activation of IRMOF-16 via solvent exchange yields a N$_2$-accessible surface area of 470 m²/g while the surface area is quadrupled via ScD activation (1910 m²/g) pursuant to the invention. Although not wishing or intending to be bound by any theory, the supercritical activation appears to eliminate solvent ($CO_2$) surface tension at temperatures and pressures above the critical point. Because of their tiny size and the relative strength of the zinc-oxygen bonds that define them, the crystalline micropores that permeate the four MOF materials tested should be resistant to collapse via capillary effects, even with solvents such as DEF and DMF. The persistence of crystallinity in solvent-exchanged MOF 6, despite its inability to adsorb nitrogen, supports this contention. Similarly, the ability to resolvate MOF 6 with DMF after nitrogen adsorption isotherms indicates preservation of micropores in nitrogen-impermeable samples. Similar behavior is seen for other MOF materials.

The Examples illustrate that treatment of four representative MOF materials with liquid and supercritical carbon dioxide pursuant to the present invention resulted in substantial, or in some cases spectacular (up to 1200%), increases in gas-accessible surface area. Thus, the present invention can be used to maximize or optimize surface areas of MOF materials for many potential applications.

Synthesis

General information. Commercial reagents were purchased from Sigma-Aldrich (ACS grade) and used as received unless otherwise noted. N,N'-dimethylformamide (DMF) was purified using a two-column solid-state purification system (Glasscontour System, Jeorg Meyer, Irvine, Calif.). Elemental analyses were performed by Atlantic Microlabs, Inc. (Norcross, Ga.). Powder X-ray diffraction (PXRD) patterns were recorded with a Rigaku XDS 2000 diffractometer using nickel-filtered Cu Kα radiation ($\lambda=1.5418$ Å). Thermogravimetric analyses (TGA) were performed on a Mettler-Toledo TGA/SDTA851e. Adsorption isotherms were measured with an Autosorb 1-MP and Quadrasorb SI from Quantachrome Instruments. Ultra-high purity grade nitrogen and hydrogen were used for all adsorption measurements. ¹H NMR and ¹³C NMR were done on a Varian Inova 400 and 500 spectrometer at 500 MHz and 125 MHz respectively. Single crystals were mounted on a Bruker SMART CCD 1000 diffractometer equipped with a graphite-monochromated MoKα ($\lambda=0.71073$ Å) radiation source in a cold nitrogen stream.

Synthesis of N,N'-Di-(2,6-dimethyl-4-benzoic acid)-1,4,5,8-naphthalenetetracarboxydiimide (ligand 1)

Prepared from 1,4,5,8-tetracarboxydianhydride (1.62 g, 6.0 mmol) and 2,6-dimethyl-4-aminobenzoic acid (2.0 g, 12.1 mmol) were combined in propionic acid (25 ml) and refluxed for 48 hrs. The reaction was allowed to cool to room temperature and water (20 ml) was added to precipitate the product. The product was collected by filtration washed with ethanol and dried in vacuo to yield 1.5 g of off-white solid. ¹H NMR ($(CD_3)_2SO$, 400 MHz) δ2.13 (s, 12H), 7.8 (s, 4H), 8.8 (s, 4H); ¹³C NMR ($(CD_3)_2SO$, 100.7 MHz) δ 18.0, 127.1, 127.9, 129.9, 131.7, 132.1, 137.0, 138.2, 162.6, 167.6; MS-MALDI-TOF (m/z): [MH+] Calcd. For $C_{32}H_{22}N_2O_8$ 563.1. found 563.4

Synthesis of N,N'-Di-(4-benzoic acid)-1,2,6,7-tetrachloroperylene-3,4,9,10-tetracarboxylic acid diimide (ligand 2)

Prepared according to Addicott, C.; Oesterling, I.; Yamamoto, T.; Mullen, K.; Stang Peter, J., J. Org. Chem. 2005, 70, 797-801, which is incorporated herein by reference to this end. Briefly, 1,6,7,8-tetrachloroperylene-3,4,9,10-tetracarboxylic acid dianhydride (1.00 g, 1.89 mmol), (2.59 g, 18.9 mmol), and propionic acid (25 mL) were stirred at 160° C. for 16 hours. After the mixture was cooled to room temperature, water was added and the precipitate was filtered and washed with a mixture of methanol/water (1:1) and dried in vacuo to yield an orange solid: ¹H NMR ($D_2SO_4$, 500 MHz) δ7.63 (d, 4H), 8.36 (d, 4H), 8.74 (s, 4H); MS-MALDI-TOF (m/z): [MH+] Calcd. 768.4. found 768.1 Terphenyl dicarboxylic acid (3), was prepared according to Campbell, T. W., J. Am. Chem. Soc. 1960, 82, 3126, which is incorporated herein by reference to this end.

Synthesis of MOF 5

Ligand 1 (0.1 g, 0.177 mmol) and $Zn(NO_3)*H_2O$ (0.16 g, 0.538 mmol) were combined with 30 ml of N,N'-Diethylformamide (DEF) and sealed in a glass vial. The vial was heated to 100° C. for 48 hrs. The resulting product was filtered and washed with DEF to yield 0.05 g amber block crystals.

Synthesis of MOF 6

Ligand 2 (0.1 g, 0.13 mmol) and $Zn(NO_3)*H_2O$ (0.15 g, 0.5 mmol) were combined in 30 ml of DMF and heated to 80° C. for 48 hrs. The resulting orange crystals were filtered and washed with DMF.

Synthesis of IRMOF-16

The synthesis procedure disclosed by Eddaoudi, M.; Kim, J.; Rosi, N.; Vodak, D.; Wachter, J.; O'Keeffe, M.; Yaghi, O. M., Science, 2002, 295, 469-472, which is incorporated herein by reference, was slightly modified in order to produce enough material for further tests. That is, ligand 3 (FIG. 1D) (0.270 g, 0.848 mmol) and $Zn(NO_3)*H_2O$ (1.01 g, 3.4 mmol) were combined in 270 ml of DMF and stirred for 12 hrs. The mixture was then portioned equally into 4 separate one liter bottles and further diluted with 300 ml of DMF. The bottles were sealed and heated at 100° C. for 48 hrs. The resulting product was filtered and washed with DMF to yield small white block crystals. Anal. Calcd. C, 58.76; H, 2.96. Found C, 57.26; H, 3.06

Synthesis of IRMOF-3

IRMOF-3 was prepared as described by Tanabe, K. K.; Wang, Z.; Cohen, S. M., J. Am. Chem. Soc. 2008, 130, 8508-8517. 5. Spek, A. L., J. Appl. Crystallogr. 2003, 36, 7-13, which is incorporated herein by reference to this end.

TABLE

| Crystal data and structure refinement for 5 | |
|---|---|
| Empirical formula | C106 H83 N8 O29 Zn4 |
| Formula weight | 2194.28 |
| Temperature | 153(2) K |
| Wavelength | 0.71073 Å |
| Crystal system | Monoclinic |
| Space group | P2(1)/c |

TABLE-continued

Crystal data and structure refinement for 5

| | |
|---|---|
| Unit cell dimensions | a = 23.275(4) Å    α = 90° |
| | b = 25.486(4) Å    β = 117.409(6)° |
| | c = 49.521(7) Å    γ = 90° |
| Volume | 26078(7) Å$^3$ |
| Z | 4 |
| Density (calculated) | 0.559 Mg/m$^3$ |
| Absorption coefficient | 0.396 mm$^{-1}$ |
| F(000) | 4508 |
| Crystal size | 0.340 × 0.083 × 0.074 mm$^3$ |
| Theta range for data collection | 0.92 to 28.91° |
| Index ranges | −31 <= h <= 31, −34 <= k <= 34, −66 <= l <= 67 |
| Reflections collected | 241409 |
| Independent reflections | 63399 [R(int) = 0.1842] |
| Completeness to theta = 28.91° | 92.2% |
| Absorption correction | Integration |
| Max. and min. transmission | 0.9742 and 0.9135 |
| Refinement method | Full-matrix least-squares on F$^2$ |
| Data/restraints/parameters | 63399/0/1340 |
| Goodness-of-fit on F$^2$ | 0.563 |
| Final R indices [I > 2sigma(I)] | R1 = 0.0692, wR2 = 0.1513 |
| R indices (all data) | R1 = 0.2194, wR2 = 0.1670 |
| Largest diff. peak and hole | 0.558 and −0.270 e · Å$^{-3}$ |

Although the invention has been described in connection with certain detailed embodiments thereof, those skilled in the art will appreciate that modifications and changes can be made therein without departing from the spirit and scope of the invention as set forth in the appended claims.

REFERENCES INCORPORATED HEREIN BY REFERENCE

1. Recent reviews: (a) Collins. D. J.: Zhou. H.-C., J. Mater. Chem. 2007, 17, 3154-3160. (b) Ferey. G., Chem. Soc. Rev. 2008, 37, 191-214.
2. For example, see: (a) Bastin. L.; Barcia, P. S.; Hurtado, E. J.; Silva, J. A. C.; Rodrigues, A. E.; Chen, B. J., Phys. Chem. C 2008, 112, 1575-1581. (b) Lee, E. Y.; Jang, S. Y.; Suh. M. P., J. Am. Chem. Soc. 2005. 127, 6374-6381. (c) Dinca, M.; Long, J. R., J. Am. Chem. Soc. 2005. 127, 9376-9377. (d) Snurr. R. Q.; Hupp, J. T.; Nguyen. S. T., AIChE 2004, 50, 1090-1095. (e) Bae, Y. S.; Mulfort. K. L.; Frost, H.; Ryan, P.; Punnathanam, S.; Broadbelt. L. J.; Hupp, J. T.; Snurr, R. Q., Langmuir 2008, 24, 8592-8598. (f) Bae, Y. S.; Farha, O. K.; Spokoyny, A. M.; Mirkin. C. A.; Hupp, J. T.; Snurr, R. Q., Chem. Commun. 2008, 4135-4137.
3. (a) Wu. C.-D.; Hu. A.; Zhang, L; Lin. W., J. Am. Chem. Soc. 2005, 127, 8940-8941. (b) Horike. S.; Dinca, M.; Tamaki. K.; Long, J. R., J. Am. Chem. Soc. 2008, 130. 5854-5855. (c) Cho, S.-H.; Ma, B.; Nguyen, S. T.; Hupp. J. T.; Albrecht-Schmitt, T. E., C'hem. Commun. 2006, 256, 3-2565.
4. For example, see: (a) Collins, D. J.; Zhou. H.-C., J. Mater. Chem. 2007, 17, 3154-3160. (b) Ferey, G., Chem. Soc. Rev. 2008, 37, 191-214. (c) Nouar, F.; Eubank. J. F.; Bousquet, T.; Wojtas, L.; Zaworotko, M. J.; Eddaoudi. M., J. Am. Chem. Soc. 2008. 130, 1833-1835. (d) Chen, B.; Ockwig, N. W.; Millard, A. R.; Contreras, D. S.; Yaghi. O. M., Angew. Chem., Int. Ed. 2005. 44, 4745-4749. (e) Dinca, M.; Dailly, A.; Liu. Y.; Brown, C. M.; Neumann. D. A.; Long. J. R., J. Am. Chem. Soc. 2006, 128, 16876-16883. (f) Latroche, M.; Surble, S.; Serre, C.; Mellot-Draznieks, C.; Llewellyn, P. L.; Lee, H.; Chang, J.; Jhung, S. H.: Ferey, G. Angew. Chem., Int. Ed. 2006, 45, 8227-8231. (g) Mulfort. K. L.; Hupp. J. T., J. Am. Chem. Soc. 2007, 129, 9604-9605. (h) Farha, O. K.; Spokoyny, A. M.; Mulfort, K. L.; Hawthorne, M. F.; Mirkin, C. A.; Hupp, J. T., J. Am. Chem. Soc. 2007, 129, 12680-12680.
5. Duren, T.; Milliange. F.; Ferey. G.; Walton. K. S.; Snurr. R. Q. J. Phy. Chem. C 2007, 111, 15350-15356.
6. (a) Kepert, C. J.; Rosseinsky, M., J. Chem. Commun. 1999, 375-376. (b) Yaghi. O. M.; Li, H.; Davis, C.; Richardson, D.; Groy, T. L., Acc. Chem. Res. 1998, 31, 474-484.
7. Eddaoudi, M.; Kim. J.; Rosi. N.; Vodak. D.; Wachter, J.; O'Keeffe, M.; Yaghi. O. M., Science 2002. 295-469-472.
8. (a) Reichenauer, G.; Scherer, G. W., Colloids Surf, A 2001, 187-188, 41-50. (b) Reichenauer, G.; Scherer. G. W., J. Non-Cryst. Solids 2001, 285, 167-174. (c) Cooper. A. I., J. Mater. Chem. 2000, 10, 207-234. (d) Lubguhan, J. A.; Gangopadhyay, S.; Lahlouh, B.; Rajagopalan, T.; Biswas, N.; Sun. J.; Huang, D. H.; Simon, S. L.; Mallikarjunan. A.; Kim, H.-C.; Hedstrom, J.; Volksen. W.; Miller, R. D.; Toney, M. F., J. Mater. Res. 2004, 19, 3224-3233.
9. (a) Wang. Z.; Cohen, S. M., J. Am. Chem. Soc. 2007, 129, 12368-12369. (b) Wang, Z.; Cohen, S. M., Angew. Chem. Int. Ed. 2008. 47, 4699-4702. (c) Tanabe, K. K.; Wang, Z.; Cohen, S. M., J. Am. Chem. Soc. 2008, 130, 8508-8517.

What is claimed is:

1. A metal-organic framework material comprising:

a plurality of metal ions or metal clusters; and a plurality of organic ligands coordinated to the plurality of metal ions or clusters, wherein the metal-organic framework material has been treated with a supercritical fluid to increase its internal surface area;

wherein the plurality of organic ligands comprises one or more of:

1

-continued

2. The metal-organic framework of claim 1, wherein the metal-organic framework comprises a nitrogen accessible surface area of at least 1910 m²/g.

3. The metal-organic framework material of claim 1, wherein:
   the metal-organic framework material includes a plurality of $Zn_4O$ clusters; and
   the plurality of organic ligands are coordinated to the plurality of $Zn_4O$ clusters.

4. The metal-organic framework material of claim 3, wherein the metal-organic framework material comprises a nitrogen-accessible surface area of more than 400 m²/g.

5. The metal-organic framework material of claim 4, wherein the metal-organic framework material comprises a nitrogen-accessible surface area of at least 1910 m²/g.

6. The metal-organic framework material of claim 5, wherein the metal-organic framework material comprises the nitrogen-accessible surface area of at least 2850 m²/g.

7. A method for the treatment of a MOF material to increase its internal surface area, comprising introducing a liquid into the MOF, subjecting the MOF to supercritical conditions to form supercritical fluid, and releasing the supercritical conditions to remove the supercritical fluid.

8. The method of claim 7, wherein the liquid is liquid carbon dioxide and the supercritical conditions exceed the critical point of carbon dioxide.

9. The method of claim 7, wherein the MOF material is subjected to supercritical conditions in a critical point dryer.

10. The method of claim 9, wherein the supercritical conditions are released by venting the critical point dryer to atmosphere.

11. The method of claim 7, further comprising:
   removing the liquid from a chamber containing the MOF during the step of subjecting the MOF to supercritical conditions; and
   filling the liquid into the chamber containing the MOF during the step of subjecting the MOF to supercritical conditions.

12. The method of claim 11, wherein the liquid is liquid carbon dioxide and the chamber comprises a drying chamber of a critical point dryer.

13. The method of claim 12, wherein the liquid is removed by venting some of the liquid under positive pressure from the drying chamber at a rate below a rate of filling the liquid into the drying chamber.

14. The method of claim 13, wherein the liquid is vented for five minutes every hour.

* * * * *